(12) United States Patent
Bruun Lauritzen et al.

(10) Patent No.: US 9,968,458 B2
(45) Date of Patent: May 15, 2018

(54) MEDICAL IMPLANT FOR REDUCING PAIN IN DISEASED JOINTS

(71) Applicant: Bispebjerg Hospital, Copenhagen NV (DK)

(72) Inventors: Jes Bruun Lauritzen, Copenhagen K (DK); Sune Lund Sporring, Næstved (DK)

(73) Assignee: Bispebjerg Hospital, Copenhagen (DK)

( * ) Notice: Subject to any disclaimer, the term of this patent is extended or adjusted under 35 U.S.C. 154(b) by 0 days. days.

(21) Appl. No.: 14/652,168

(22) PCT Filed: Dec. 18, 2013

(86) PCT No.: PCT/DK2013/050438
§ 371 (c)(1),
(2) Date: Jun. 15, 2015

(87) PCT Pub. No.: WO2014/094785
PCT Pub. Date: Jun. 26, 2014

(65) Prior Publication Data
US 2015/0335437 A1    Nov. 26, 2015

(30) Foreign Application Priority Data
Dec. 18, 2013 (DK) .................................. 2012 70790

(51) Int. Cl.
*A61F 2/36* (2006.01)
*A61B 17/16* (2006.01)
(Continued)

(52) U.S. Cl.
CPC ........ *A61F 2/3609* (2013.01); *A61B 17/1668* (2013.01); *A61F 2/30756* (2013.01);
(Continued)

(58) Field of Classification Search
CPC ........ A61F 2/36; A61F 2/3601; A61F 2/3603; A61F 2/3607; A61F 2/3609;
(Continued)

(56) References Cited

U.S. PATENT DOCUMENTS 3,053,251 A * 9/1962 Black .................... A61F 2/3603
623/23.12
2002/0040245 A1 4/2002 Lester et al.
(Continued)

FOREIGN PATENT DOCUMENTS

DE 876739 5/1953
EP 0017930 10/1980
(Continued)

*Primary Examiner* — Brian Dukert
(74) *Attorney, Agent, or Firm* — Posternak Blankstein & Lund LLP

(57) ABSTRACT

The present invention relates to a medical implant for reducing pain in diseased joints such as synovial joints, in particular ball and socket joints such as the hip joint and the shoulder joint. One embodiment relates to a medical implant for attachment to and at least partly covering the femoral head, said medical implant comprising a dome shaped shell with an orifice, said shell having a height $h_1$, an equatorial shell radius $r_s$ and an orifice radius $r_o$ wherein the shell radius $r_s > r_o$, and $h_1 > r_s$, and the orifice is defined by a circumferential rounded edge.

29 Claims, 11 Drawing Sheets

(51) Int. Cl.
   *A61F 2/30*       (2006.01)
   *A61F 2/34*       (2006.01)
(52) U.S. Cl.
   CPC .............. *A61F 2/34* (2013.01); *A61F 2/3603* (2013.01); *A61F 2002/30703* (2013.01); *A61F 2002/30705* (2013.01); *A61F 2002/30757* (2013.01); *A61F 2210/0076* (2013.01); *A61F 2230/0093* (2013.01)
(58) Field of Classification Search
   CPC ...... A61F 2002/3605; A61F 2002/3611; A61F 2002/30703; A61F 2002/4007
   See application file for complete search history.

(56) References Cited

U.S. PATENT DOCUMENTS

| | | |
|---|---|---|
| 2005/0085915 A1 | 4/2005 | Steinberg |
| 2009/0048679 A1 | 2/2009 | Howald et al. |
| 2009/0187252 A1 | 7/2009 | Howald et al. |
| 2012/0109334 A1 | 5/2012 | Forsell |

FOREIGN PATENT DOCUMENTS

| | | |
|---|---|---|
| EP | 1872745 | 1/2008 |
| FR | 2847458 | 5/2004 |
| WO | WO 2006/133711 | 12/2006 |
| WO | WO 20071121167 | 10/2007 |

* cited by examiner

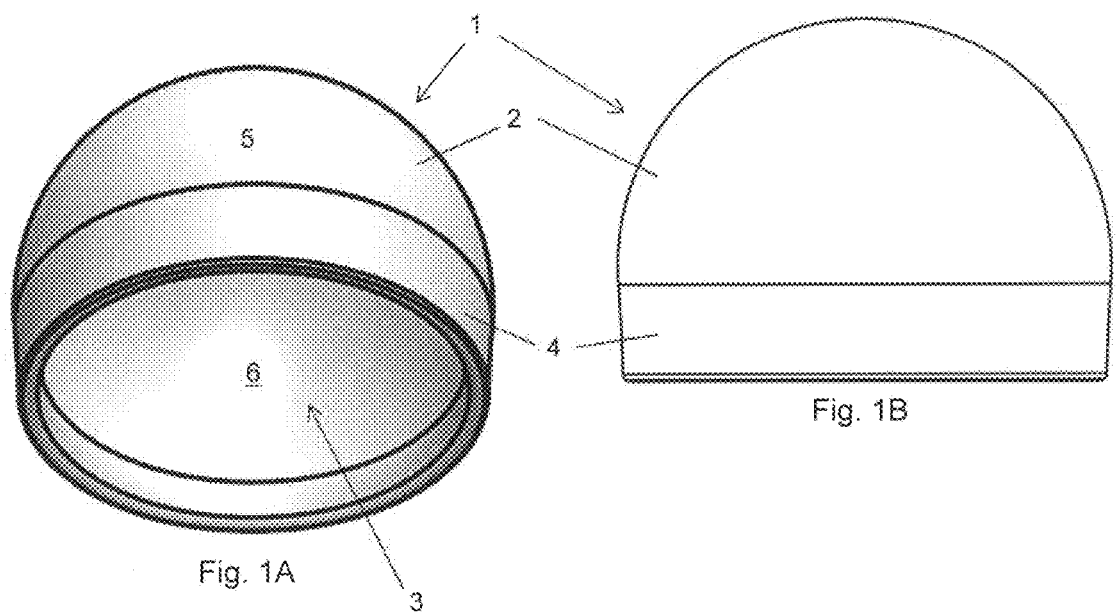
Fig. 1A
Fig. 1B
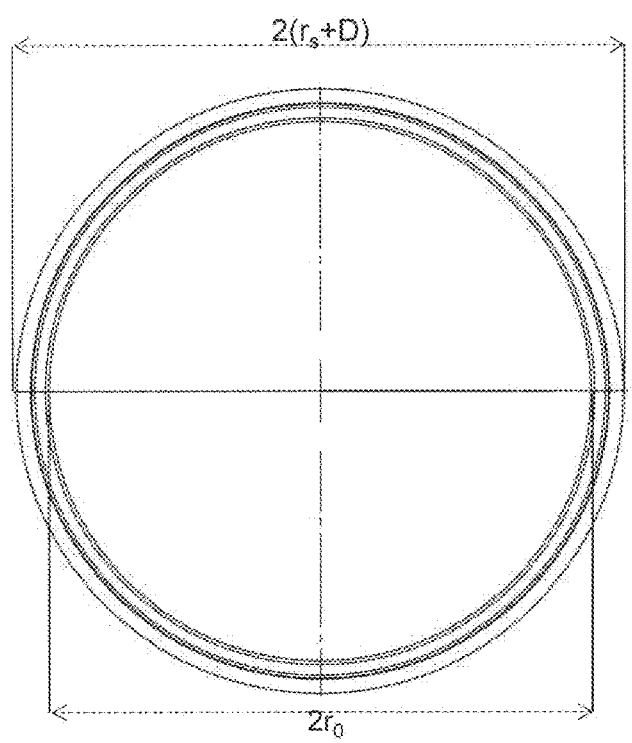
Fig. 2

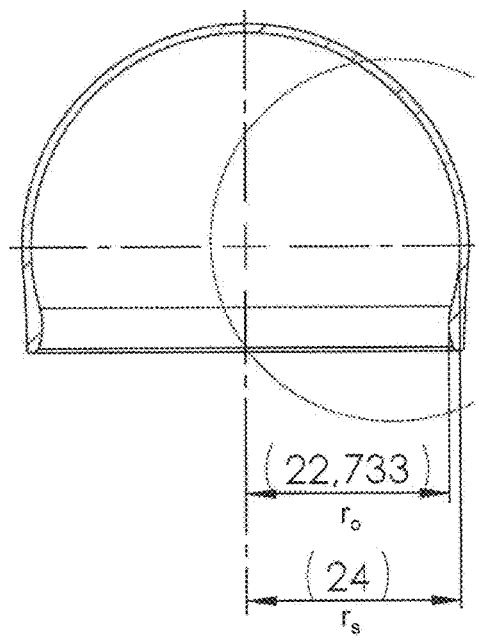 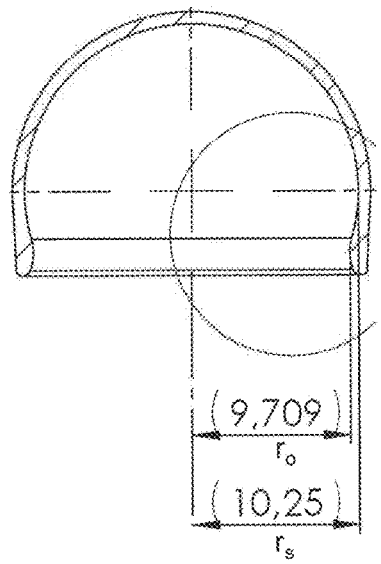
Fig. 5A  Fig. 5B
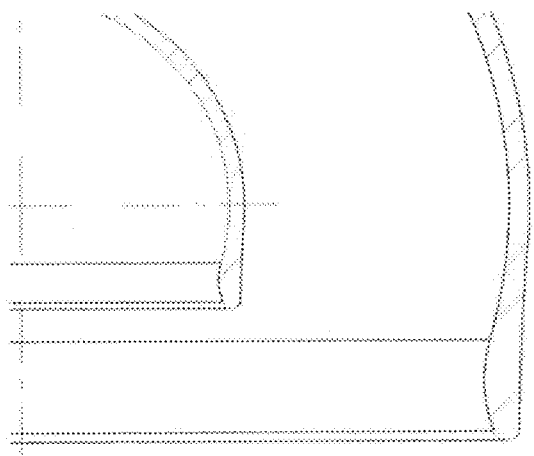 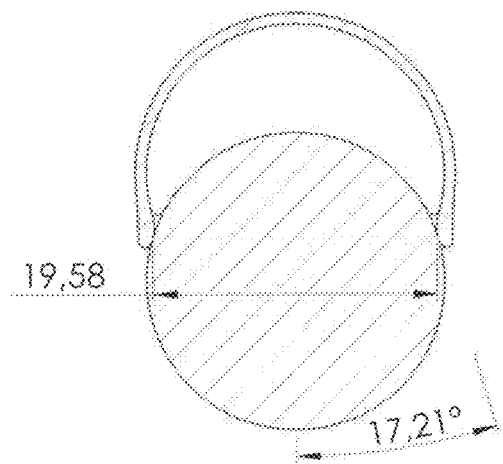
Fig. 6  Fig. 7

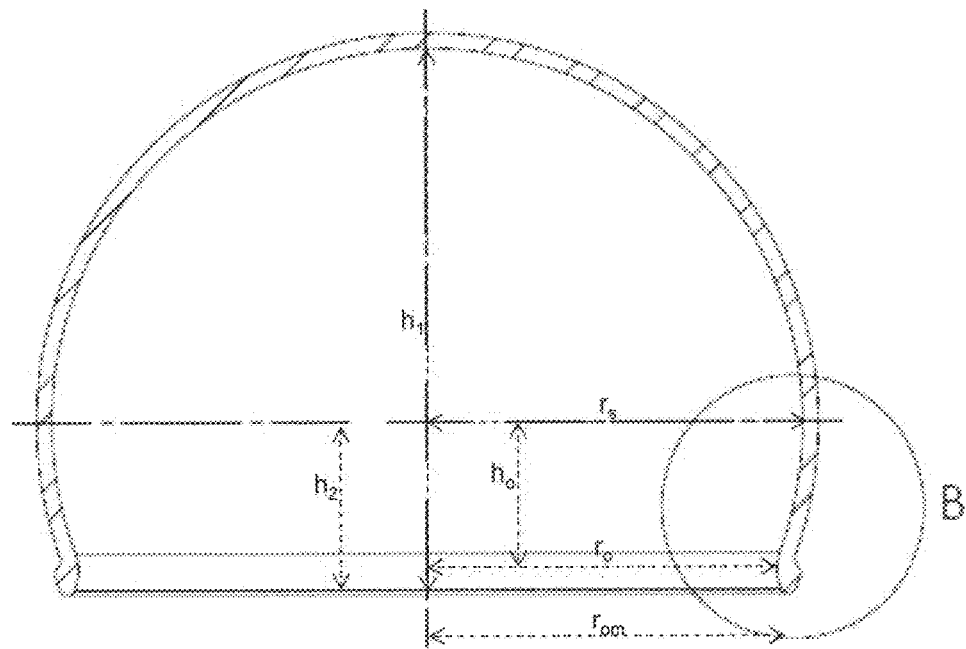
Fig. 9B
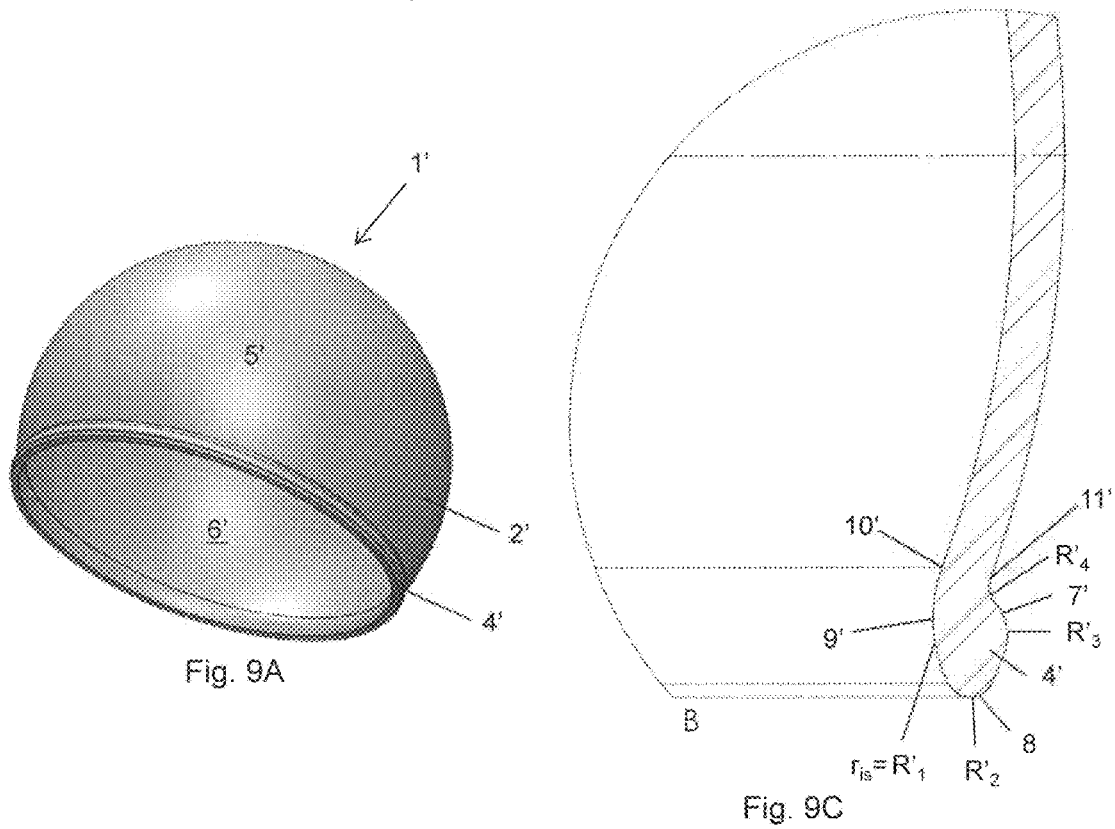
Fig. 9A
Fig. 9C

MEDICAL IMPLANT FOR REDUCING PAIN IN DISEASED JOINTS

The present invention relates to a medical implant for reducing pain in diseased joints such as synovial joints, in particular ball and socket joints such as the hip joint and the shoulder joint.

BACKGROUND OF INVENTION

Joint damage, such as cartilage damage, is often treated by replacing the joint with an artificial joint. However, complications may be caused by the replacement by artificial joints, in particular a high occurrence rate of loosening problems that may result in breakage of the bones around the artificial joint.

In particular, the invasive character of the fixation of the prostheses such as cementing or anchoring of the prosthesis with screws and pins result in side-effects such as risk of infection, loosening as mentioned above as well as luxation of the artificial hip joint, or periprosthetic fractures, damage on bone or interruption of blood supply possibly leading to necrosis.

Manufacturers of prosthetic medical implants constantly work toward developing better products by improving their physical properties. Improved wear resistance, for example, is a desirable quality to impart to a prosthetic medical device. However, the inherent designs of existing implants has not solved these problems, and problems persist with e.g. wear and creation of small particles released from one or more parts of the implants. The particles are liberated from the implant or the cement as abrasion caused by the motion of the implant and friction against other components within the body. The known Smith-Petersen implants from the first half of the 20$^{th}$ century had problems with fixation and impingement due to the design of implants and the patient selection criteria.

Thus, a need for improved prosthetic medical devices with fewer complications and improved wear resistance exists. Also there is a need for an implant which requires a minimal surgical intervention to the bone of the joint and the various tissues in the area.

SUMMARY OF INVENTION

Therefore, the purpose of the present invention is to provide an implant which requires a lesser intervention to and around the diseased joint and natural bone structure, which limits the expenses in relation to e.g. hip surgery; preferably an implant that can at least delay the need for a full joint replacement, preferably for a minimum of 5 years.

These and other advantages are achieved by the presently disclosed medical implant for attachment to and at least partly covering the femoral head, said medical implant comprising a dome shaped shell with an orifice, said shell having a height $h_1$, an equatorial shell radius $r_s$ and an orifice radius $r_o$ wherein the (inner) equatorial shell radius $r_s$ is larger than the (inner) orifice radius $r_o$ (radius $r_s>r_o$), and the (inner) height $h_1$ is larger than the equatorial shell radius $r_s$ (height $h_1>r_s$), and the orifice is defined by a circumferential rounded edge, thus forming an interpositional, intraarticular shell which covers the femoral head anatomically thereby relieving the discomfort caused by the friction related pain between the femoral head and pelvis during movement of a diseased joint. The discomfort is relieved as both the surface of the femoral head and the surface of the acetabulum abuts the surface of the shell; the inner and outer surface of the shell respectively, thereby reducing the friction in the joint. A preferred embodiment relates to a medical implant for attachment to and at least partly covering the femoral head, said medical implant comprising a dome shaped shell with skirt zone below the equatorial plane having an orifice, said shell having a height $h_1$, an equatorial shell radius $r_s$ and an orifice radius $r_o$ wherein the shell radius $r_s>r_o$, and $h_1>r_s$, the orifice is defined by a circumferential rounded edge, and the inner surface of the shell of at least a part of said skirt zone has a different curvature than the curvature of the inner surface of the shell above the equatorial plane.

The way the shell of the implant fits around the femoral head makes it possible that the implant is at least initially unconstrained when attached. Hence, the presently disclosed medical implant is preferably configured and/or arranged for at least initial unconstrained attachment to the natural femoral head. The implant can be press fit to a shaped femoral head and held in place by negative pressure and counter-pressure from acetabulum. Initially after insertion of the medical implant in a subject, the femoral head and the acetabulum can move against a smooth surface of the implant. The implant can thus be free to rotate relative to the femoral head as there is no risk that the implant is detached or misaligned due to the shape of the implant.

An unconstrained implant may be pushed to rotate relative to the joint parts by the natural motion of the hip thereby relieving friction even further. The implant may become attached to either the femoral head or the acetabulum by natural growth of different types of tissue over time, but the shell will remain able to provide pain relief to the joint as it will still be preventing (or at least reducing) friction between the femoral head and the acetabulum. If it becomes attached to the femoral head, the movement is between the acetabulum and the smooth outer surface of the medical implant, whereas if it becomes attached to the acetabulum the femoral head can move against the smooth inner surface of the medical implant. If the shell becomes attached it may in most cases be to the femoral head.

As the implant preferably is at least initially unrestrained, i.e. allowed to rotate and tilt with respect to the axis of the femoral neck, the implant can be allowed to become attached to the femoral head or acetabulum in a position which is adapted to the joint, as it may become attached in a position which is "naturally selected" by the motion pattern, geometry and forces of the specific joint.

The dome is preferably a spherical dome, i.e. at least part of the shell may be spherical. The shell is furthermore preferably spherical to a position below the equatorial plane (aka the great circle of the shell. The medical implant preferably comprises a skirt zone below the equatorial plane of the shell. The properties of the skirt zone may be the same as the properties of the main shell. However, the implant may be configured such that the skirt zone has other properties, e.g. in terms of flexibility, thickness or curvature of the shell. The skirt zone may have properties selected to make attachment easier e.g. be flexible, have a specific surface, smooth etc. The skirt zone can also have properties which helps protect the femoral neck and surrounding tissue e.g. smooth surface and/or soft shape. The skirt zone can extend from the orifice towards the equator of the shell and can comprise at least the collar and the orifice. The inner surface of the shell and/or the outer surface of the shell of at least a part of said skirt zone may have a different curvature than the curvature of the shell above the equatorial plane. This change in curvature helps to the orifice such that the implant can be attached to the natural femoral head. Due to the shape of the femoral head and the shells dome shape where the equatorial radius of the shell is larger the radius of the orifice and where the height of the shell is larger than the equatorial radius of the shell, the shell can be pressed over the femoral head at a specified angle and thereby be attached as it encircles the dome of the femoral head and extends below the femoral head where the orifice encircles the femoral neck.

Thus, the presently disclosed medical implant is arranged to allow the shell to be attached around the femoral head from where it cannot be disengaged during normal hip alignment and movement as the diameter of the orifice of the shell is smaller than the largest diameter of the femoral head. When the implant is attached to the femoral head the orifice is below the femoral head i.e. it encircles part of the femur neck near the femoral head wherefore the rounded edge is an advantage as it prevents damage to the bone and tissue done by the edge of the orifice.

Due to the shape of the shell there may be no need to e.g. press or otherwise deform the orifice to make the edge of the orifice "squeeze" around the femur head when attached to the femoral head.

The implant of the present disclosure is advantageously used in cases of degenerative joint diseases like arthritis, where the natural cartilage and/or bone is damaged and the disease is associated with pain. The implant can be used in humans as well as in animals for example dogs and horses. The dimensions such as material thickness and shell radius and height may be varied to fit a specific size of femoral head.

The presently disclosed medical implant preferably comprises an unbroken surface.

In a further embodiment of the presently disclosed implant only the inner surface of the shell is smooth and spherical whereas the outer surface is precisely adapted to the shape of the acetabulum of the subject receiving the implant and the implant is therefore also adapted to be attached to the acetabulum such that the movement is provided between a smooth inner surface of the implant and the femoral head. Similarly only the outer surface of the shell may be smooth and spherical whereas the inner surface is precisely adapted to the shape of the femoral head of the subject receiving the implant and the implant is therefore also adapted to be attached to the femoral head such that the movement is provided between a smooth outer surface of the implant and the acetabulum.

The presently disclosed medical implant may also be applied to other synovial joints, in particular ball and socket joints, such as the shoulder joint. Thus, as herein described the term "femoral head" may be replaced by the term "humeral head", such that the presently disclosed medical implant in a further embodiment is suitable for attachment to and at least partly covering the humeral head and comprising any of the herein disclosed features.

DESCRIPTION OF DRAWINGS

In the following the invention is further described with respect to a number of drawings. The drawings are exemplary and are not to be construed as limiting to the invention.

FIGS. 1-8 illustrate various details of one embodiment of the presently disclosed implant.

FIG. 1*a* shows a perspective view of one embodiment of the implant according to the present disclosure.

FIG. 1*b* shows a side view of the implant in FIG. 1*a*.

FIG. 2 shows one embodiment of the implant from the direction of the orifice.

FIG. 5*a* shows a midpoint sectional view of the implant in FIG. 4*a* indicating the size of $r_o$ and $r_s$.

FIG. 5*b* shows a midpoint sectional view of the implant in FIG. 4*b* indicating the size of $r_o$ and $r_s$.

FIG. 6 compares the size of the implants in FIGS. 5*a* and 5*b*.

FIG. 7 illustrates how the implant in FIG. 5*b* impinges on a sphere with an outside diameter equal to inside shell diameter of the implant.

FIGS. 9 and 10 show various details of a second embodiment of the presently disclosed implant, where FIG. 9*a* shows a perspective view of the implant according to the present disclosure.

FIG. 9*b* shows a midpoint sectional view of the implant in FIG. 9*a*.

FIG. 9*c* shows a close-up of the cut-out indicated by B in FIG. 9*b*.

DETAILED DESCRIPTION OF THE INVENTION

Figure 3A:
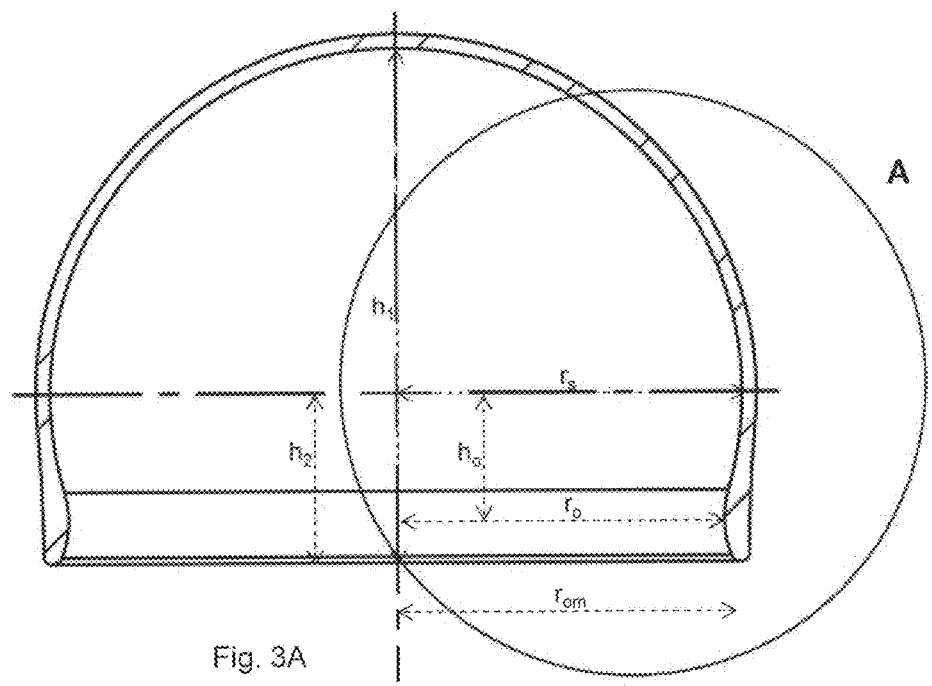
FIG. 3*a* shows a midpoint sectional side view of the implant in FIG. 1.

As previously stated the dome is preferably a spherical dome or at least substantially a spherical dome as this shape fits around the natural femoral head and matches the spherical shape of the acetabulum. Further, a spherical curvature may provide a highly stable and stiff structure to at least the upper hemisphere of the shell. In other embodiments the shell can be other shapes, e.g. a more elliptical dome if this is preferred to obtain a better fit around a femoral head with a less rounded shape.

In one embodiment of the presently disclosed implant the inside surface of the shell is spherical to a first position below the equatorial plane. This first position may be seen as the intersection between a circle and the shell below the equatorial plane. The curvature of the inner surface preferably changes sign at this first position. The inner surface may thus curve in the opposite direction below said first position compared to the curvature of the inner surface above this first position. This first position may also be an inflection point of the inner surface of the shell. An inflection point (or point of inflection) is normally defined as a point on a curve at which the curvature or concavity changes sign from plus to minus or from minus to plus, i.e. the curve changes from being concave upwards (positive curvature) to concave downwards (negative curvature), or vice versa. The first position may also be seen as an anticlastic point of the inner surface. An anticlastic point of a surface is normally defined as having a curvature in a particular direction that is of the opposite sign to the curvature at that point in a perpendicular direction.

In one embodiment this first position is located at least 5° below the equatorial line, or at least 7°, or at least 10°, or at least 11°, or at least 12°, or at least 13°, or at least 14°, or at least 15°, or at least 16° below the equatorial line. Furthermore, the first position may be located less than 20° below the equatorial line, or less than 19°, or less than 18°, or less than 17° below the equatorial line.

A sphere has a constant radius of curvature, i.e. for a spherical shell with a radius $r_s$ and a constant thickness D, the inner surface of the spherical shell has a radius of curvature of $r_s$, whereas the outer surface of the shell has a radius of curvature of $r_s+D$. Thus, as previously stated the shell of the presently disclosed implant may be at least partly spherical to a point below the equator. Hence, in a further embodiment the radius of curvature of the inner surface of the shell changes from $r_s$ to $r_{is}$ at the first position, and wherein $r_s/r_{is}$ is between 2.8 and 4, or between 3 and 3.8, or between 3.2 and 3.6, or between 3.3 and 3.5, or between 3.35 or 3.45, or between, 3.4 and 3.45. Examples of this change in curvature are illustrated in detail in FIGS. 3b, 4a, 4b, 9c and 9d.

Correspondingly the outside surface of the shell may be spherical to a second position below the equatorial plane. The curvature of the outer surface preferably changes sign at this second position. I.e. the outer surface may curve in the opposite direction below said second position. Correspondingly the second position may be seen as an inflection point of the outer shell surface. Further, the second position may be seen an anticlastic point of the outer shell surface. The first and second positions may be aligned, but in most cases they are at different positions relative to the equatorial plane.

In one embodiment this second position is located at least 1° below the equatorial plane, or at least 2°, or at least 3°, or at least 4°, or at least 5° below the equatorial line. Further, the second position may be located less than 25° below the equatorial plane, or less than 22°, or less than 21°, or less than 20°, or less than 18°, or less than 15°, or less than 12°, or less than 10°, or less than 9°, or less than 8°, or less than 7°, or less than 6°, or less than 5° below the equatorial line. Further, this second position may be located at least 15° below the equatorial plane, or at least 16°, or at least 17°, or at least 18°, or at least 19° below the equatorial line.

As also may be the case for the inner position, the radius of curvature of the outer surface of the shell may be changing from $(r_s+D)$ to $r_{os}$ at said second position, and wherein $(r_s+D)/r_{os}$ is less than 1, or less than 0.8, or less than 0.6, or less than 0.4, or less than 0.35, or less than 0.3, or less than 0.28, or less than 0.27 or less than 0.26, or less than 0.25, or less than 0.2, or less than 0.15, where D is the thickness of the shell.

In a further embodiment of the presently disclosed implant the thickness of the shell is constant above said first position and wherein the thickness of the shell is varying below said first position. For example the maximum thickness of the shell above said first position is less than the maximum thickness of the shell below said first position. Correspondingly the thickness of the shell may be constant above said second position and wherein the thickness of the shell is varying below said second position. For example the maximum thickness of the shell above said second position is less than the maximum thickness of the shell below said second position.

The lower height $h_2$, is the distance from the equatorial plane containing the equatorial shell radius $r_s$ to the plane of the maximal orifice radius $r_{om}$. I.e. $h_2$ indicate how far below the equator the dome+collar is extending. The ratio between the height $h_1$ and the lower height $h_2$ ($h_1:h_2$) is preferably between 2.8 and 4 depending on e.g. the dimensions of the collar and on how far the dome incl. collar extends below the equatorial plane. In a further embodiment the factor $h_1/r_s$ is at least 1.47, or at least 1.48, or at least 1.49. Further, $h_1/r_s$ may be at less than 1.65, or less than 1.62, or less than 1.6, or less than 1.58, or less than 1.57, or less than 1.55, or less than 1.54, or less than 1.53, or less than 1.52, or less than 1.51. Even further $h_1/r_s$ may be between 1.2 and 1.7, or between 1.4 and 1.6, or between 1.45 and 1.55, or between 1.47 and 1.53, or between 1.48 and 1.52, or between 1.49 and 1.51.

$h_o$ is the distance from the equatorial plane to the plane comprising the orifice diameter $r_o$. If the collar does not extend below or substantially below the main dome $h_2$ is at least approximately equal to $h_o$.

The maximal orifice radius $r_{om}$ is preferably approximately equal to or larger than the equatorial radius $r_s$ in order to enable as easy an attachment as possible. The factor $r_{om}/r_s$ may be between 0.95 and 1.05, or between 0.96 and 1.04, or between 0.97 and 1.03, or between 0.98 and 1.02, or between 0.99 and 1.015. However, $r_o$ is less than $r_{om}$, hence $r_o/r_{om}$ may be less than 0.98, or less than 0.98, or less than 0.97, or less than 0.96, or less than less than 0.95, or less than 0.94, or less than 0.93.

For example in an implant suiting a dog the height $h_1$ is 19.78 mm, $h_2$=6.28 mm, $h_o$ (the distance from equator to the plane comprising the smallest diameter $r_o$) is approximately 4.6 mm, the equatorial shell radius $r_s$=13.5 mm and the (smallest) orifice radius $r_o$ is 12.83 mm. The ratio between $r_s$ and $r_o$, $r_o/r_s$ is thus 0.95 in this example.

The distance $h_o$ is an indication of how far below the equatorial plane the basic dome shell (i.e. without the collar) extends. The difference between $h_o$ and $h_2$ is an indication of how far the collar extends below the orifice plane containing $r_o$.

The equatorial diameter ($2r_s$) is preferably between 35 and 55 mm for women, 40-65 mm for men, 10-30 mm for dogs, 50-150 for horses, depending on the maximum diameter of the femoral head. The other parameters $h_1$, $h_o$, $h_2$, $r_o$, $r_{om}$ may vary accordingly and may preferably be varied with respect to each and $r_s$ to at least approximately maintain relationships as exemplified above.

Preferably the ratio $r_o/r_s$ between the equatorial radius $r_s$ and the orifice radius $r_o$ is between 0.98 and 0.90 or e.g. between 0.97 and 0.92. Or specified reversely: The factor $r_s/r_o$ may be at least 1.02, or at least 1.03, or at least 1.04, or at least 1.05, or at least 1.053. Implants according to the present invention can be manufactured in a variety of size combinations i.e. for a give equatorial radius several different embodiments with different orifice radius is possible. This can for example be an advantage in order to accommodate joints with different relations between the largest and smallest diameter of the femoral head.

In embodiments where the rounded edge forms a collar or is part of a collar encircling the orifice the collar can provide different features to the shell. For example the edge or collar can be arranged to function as an engagement point for a tool assisting attachment and/or detachment of the implant.

In one embodiment the rounded edge/collar is curving outward to form an orifice with a maximum radius $r_{om}$ and a minimum radius equal to the orifice radius $r_o$. When the rounded edge/collar is curving outward a smooth rounded inner surface may be formed on the inner side of the collar, which smooth rounded inner surface and larger maximum orifice diameter may enable an attachment of the implant with less force.

Depending on the collars shape on the outer surface of the implant the collar can be arranged to limit the motion of the implant for example so that the collar will engage against the acetabulum when the implant is tilted too far with respect to the axis of the femoral neck thus preventing an undesirable angling of the implant relatively to the femoral head and neck. For example if the collar is thick relative to the average shell thickness and the radius of the curvature of the inner surface of the collar is larger than the radius of the outer surface of the collar, a curve with a small radius can be formed at the border between the shell and the collar thus forming a circumferential shoulder. This shoulder can be used to define the implants maximum tilt as it may abut the acetabulum at selected angels. Also this shoulder can be used for engagement of tools during the attachment, correction and/or removal of the implant. The provision of this collar is however a balance between the advantages provided during attachment of the implant and the prevention of undesirable angles and the risk of the collar interfering with the acetabulum possibly causing discomfort for the patient.

During the attachment process it can be advantageous if the medical implant is flexible preferably at a collar and/or skirt zone including the orifice. If the skirt zone is at least partly flexible the implant can be reversibly deformed during the attachment process in order to allow the implant to slide over the femoral head to its intended position with less friction compared to an un-deformed implant. The deformation can be made by the force of fingers or of a tool. When the force is relieved the original shape of the implant is at least partly restored. When the force is relieved the original shape of the implant is preferably restored.

The thickness D of the shell can be between 0.1 and 1.5 mm, or between 0.5 and 0.6 mm, or between 0.6 and 0.7 mm, or between 0.7 and 0.8 mm, or between 0.8 and 0.9 mm, or between 0.9 and 1.0 mm, or between 1.0 and 1.1 mm, or between 1.1 and 1.2 mm, or between 1.2 and 1.3 mm, or between 1.3 and 1.4 mm, or between 1.4 and 1.5 mm, or between 1.5 and 2.5 mm or even op to between 4 and 5 mm. This thickness D may be the thickness of the part of the shell that has a constant thickness. The thickness of the shell is chosen in order to provide a strong implant which can fit between the femoral head and the acetabulum without causing unintended pressure or stress to any parts of the joint. The thickness can be chosen to ensure that the implant does not deteriorate as result of the friction against femoral head and/or the acetabulum as well as it can be chosen to ensure a certain stiffness of the implant. A too thin shell may result in a less stiff and/or a shell in risk of deteriorating. A too thick shell may cause discomfort and excessive pressure on parts of the joint.

In some embodiments the thickness of the shell varies in order to obtain optimized physical properties of the shell. For example the thickness of the shell can be thicker near the rounded edge and/or in the collar and/or skirt zone than at the apex (point of curvature) or upper hemisphere of the shell.

In some embodiments the lower part of the shell is provided with flaps formed by a plurality of equidistant cut-outs/slots extending from the rounded edge towards equator of the shell. These flaps can be arranged to allow the implanted to be pushed over the femoral head with less force as they allow the effective radius of the orifice to be enlarged during the attachment procedure.

The number of flaps can be 2, 3, 4, 5, 6, 7, 8, 9, 10, 11, 12, 13, 14, 15, 16, 17, 18, 19, 20, 21, 22, 23, 24, 25, 26, 27, 28, 29 or at least 30.

If e.g. the skirt zone or collar has two, three or four slits perpendicular to the orifice plane the skirt zone or collar thus has two, three or four flaps respectively which may provide some flexibility to the orifice, collar and/or skirt zone during attachments without providing too many edges which may cause irritation to tissue or compromise the physical strength of the implant. If the flaps are bendable they can be bend to ensure an improved fit of the implant around the femoral neck. The flaps can be adapted to be bended by a tool which may allow a faster attachment procedure requiring less force applied by the surgeon.

In some embodiments the implant according to the present invention consists of two or more parts which prior to or during the attachment procedure are attached to each other to form the implant.

In several preferred embodiments the implant is a single piece unit thereby providing an implant which may have less risk of disintegrating due to wear and which in general may be more stiff and/or durable than multipart implants.

Preferably the implant is made of a durable material which can provide a smooth surface between the femoral head and the acetabulum in order to minimize friction in the diseased joint during movement of the hip. The material can advantageously be chosen to be resilient to the constant pressure applied by the joint parts during joint movement in order not to allow abrasion of particles from the implant as well as to prevent disintegration of the implant such as fractions.

Preferably the material is biocompatible and/or does not (or at least reduced and minimal) release of undesired particles (including ions and atoms) by abrasion or by diffusion from material to tissue. For example the shell/casing can be metallic as metals can provide an implant with a high degree of structural strength which does not wear down easily. If the shell/casing is manufactured in a steel alloy, such as 316 LVM steel a strong shell with a minimal risk of corrosion is provided. Alternatively the shell/casing is manufactured in a cobalt/chromium alloy or in a titanium alloy. It is also possible that the shell/casing is manufactured in a polymer or a reinforced polymer material.

In some embodiments the shell is made of a layered material whereby specific properties can be provided to e.g. the inner and outer side of the shell. A layered material can be a material wherein the layers are separate specific layers and/or a material wherein two surfacing layers are entangled at least in a region between said two surfacing materials. Layered materials and interfaces between layers may also comprise covalent or other chemical bindings binding the layers together and/or otherwise stabilising the structure and/or layers.

For example the shell can comprise at least one coating layer provided to obtain one or more specific properties on one or more surfaces of the implant. For example a hydrophilic coating layer or another coating layer which can lower the friction between implant and femur head, can advantageously be provided to the inner surface or part of the inners surface and/or rounded edge in order make the attachment process require less force. Hydrophilic layers which are non toxic exists allowing for application of hydrophilic layers which can be advantageous during the attachment procedure and which can slowly dissolve or be worn off without any potential risks to the patient. Such hydrophilic layers may e.g. include polyvinylpyrrolidone and/or polyamides. A coating layer can also be a reinforcing coating layer to render the surface less prone to erosion, reactions, degradation and/or other damages to the implant caused by use even prolonged use.

An implant for replacement within a joint should preferably enable the normal function and movements of the joint. Weight-bearing joints, in which movement in more than one direction takes place, are normally rather difficult to replace. During walking, the normal movement of for example the hip joint corresponds to about 37°-41° flexion/extension, 2°-14° adduction/abduction and a rotation of about 2°-16°. During movement from standing to sitting position a flexion of hip joint corresponds to a movement from 0 to 90°. When studying the movement of femoral caput to the acetabulum the latter movement includes a rotation of 90°.

Traditional two-part hip implants limit the possible range of motion for the patient due to the geometry. If the angle of the hip becomes larger than a specific there is an imminent risk that the hip will dislocate. This means that traditional hip implants requires the patient to be in full control at all times, and thus cannot be used for frail elderly and cognitive dysfunctional patients. Further the limited motion allowed in traditional two part implants means that they prevents the patient to be fully physically active often rendering them problematic in relation to young patients.

The present invention provides an implant which enables full range of motion of the joint. This is at least due to the fact that the size/geometry of the femoral head is maintained with the present implant. Thus, an implant may be provided which is bone conserving as no intervention in the femur bone or acetabulum is needed. The presently disclosed medical implant can postpone or eliminate the need for total hip replacement.

Due to the special form of the present implant wherein the dome shape enables attachment to the femur head without the need for cement end without the need for physical intervention in the bone results in reduced long term complications: No loosening of prosthesis, no cement, no prosthesis luxation.

As discussed above the present invention allows full range of motion of the hip joint similar to that of a healthy joint. The full range of motion is provided as the present invention as it provides a geometry of the moving parts of the joint similar to that of a natural hip. The provided range of motion provides extended inclusion criteria making the implant available and relevant for an extended group of patients including young physically active patients, frail elderly and cognitive dysfunctional patients The present invention also relates to a method for attaching a medical implant comprising the steps of attaching the medical implant from beneath the front of the femoral head close to the calcar part of same, i.e. a medical implant as disclosed herein. More specifically the implant can be attached via the smallest diameter of the femoral head, which means positioning the orifice of the implant on the femoral head just below the fovea capitis and applying force by e.g. hammering or pressing. The surgical approach can be e.g. either posterior (Moore or Southern) or anterolateral (Smith-Petersen).

If necessary due to the shape of the femoral head the method may further comprise the step of reaming the femoral head in order to remove any protrusions on the femoral head which may cause problems in relation to attachment and long term wear of the implant.

The appropriate size of the implant can be determined a method of determining the effective size of the femoral head comprising the steps of performing X-ray measurements, CT-scans and/or MR scans along two different planes, and selecting the largest diameter of the femoral head based on the measurements. Preferably the measurements are performed along the coronial plane and the sagittal plane of the human body.

X-rays can include a standard or set of standards so exact size in mm of diameter of the femoral head can be determined for proper size of implant.

Also a set of trial implants of various sizes can be provided which may be used for preoperative determination of the optimize implant fit. The trial implant is removed before the insertion of the actual implant. The most likely set of trial implants can be selected by the method of determining the effective size of the femoral head. The trial implants can be arranged to allow attachment on the femoral head with less force. Generally the use of the smallest possible implant is preferred.

It some situations it may be advantageous to reversibly deform the medical implant to an at least partly elliptic shape prior to attachment onto the femoral head e.g. by applying pressure by the fingers holding the shell or by a tool. When the implant is deformed to a more elliptical orifice and skirt it may be pushed over the femoral head to its intended position enclosing the femoral head. If the deformation is reversible the implant returns at least partly to its original shape in order to provide a smooth surface between the femoral head and the acetabulum and a rounded collar encircling the femoral neck without causing irritation and or damage to tissue or bone.

DETAILED DESCRIPTION OF THE DRAWINGS

FIGS. 1a and 1b shows an exemplary medical implant 1 according to the present invention with a perspective view in FIG. 1a and a side view in FIG. 1b. The implant comprises a dome shaped shell 2 having an orifice 3 surrounded by a skirt zone 4. The shell has an outer surface 5 and an inner surface 6. The shell 2 is spherical above the skirt zone 4.

FIG. 2 shows an implant seen from the orifice. The smallest inner diameter of the orifice is $2r_o$. The largest outer diameter is two times the equatorial radius $r_s$+the thickness D of the shell at the bottom of the shell. In the present example the orifice is a circular opening and the collar is circumferential structure.

FIG. 3a shows a cross sectional view of the implant 1 in FIG. 1. The height $h_1$ of the shell 2 is the distance from the apex of the inner surface of the shell 2 to the plane of the maximum orifice radius $r_{om}$. The lower height $h_2$, is the distance from the equatorial plane containing the equatorial radius $r_s$ to the plane of the maximum orifice radius $r_{om}$. $h_o$ is the distance from the equatorial plane to the plane of the minimum orifice radius $r_o$ $r_o$ is the smallest orifice diameter and $r_{om}$ is the maximal orifice diameter.

Figure 3B:
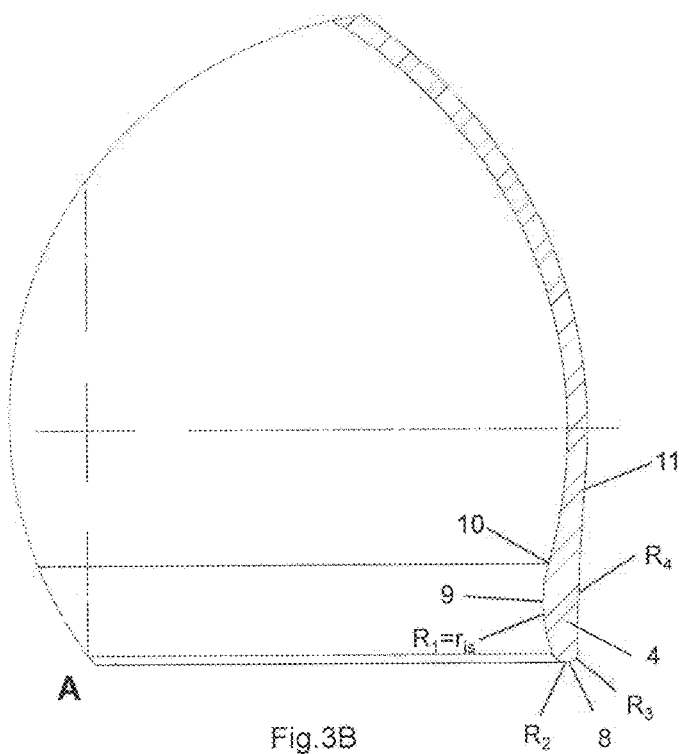
FIG. 3*b* shows a close-up of the area indicated by A in FIG. 3*a*.

FIG. 3b shows an enlargement of the section A indicated in FIG. 3a. The equatorial line is indicated by the stippled horizontal line. The skirt zone 4 is below the equator. The inner surface of the shell is spherical down to the first position 10. At this first position the inner surface of the shell begins to curve in the opposite direction (i.e. the curvature changes sign) forming an inner "collar" 9 by means of the curvature $R_1$. The curvature $R_1$ of the skirt zone "opens" the shell. The orifice is encircled by a rounded edge formed by two different radii of curvature $R_2$, $R_3$. The outer surface of the shell is spherical to a second position 11 where the outer surface begins to curve in the opposite direction by means of the curvature $R_4$. The configuration of the first and second positions and the curvatures R1, R2, R3 and R4 forms the skirt zone of the shell and determines the varying thickness of the shell at the skirt zone.

Figure 4A:
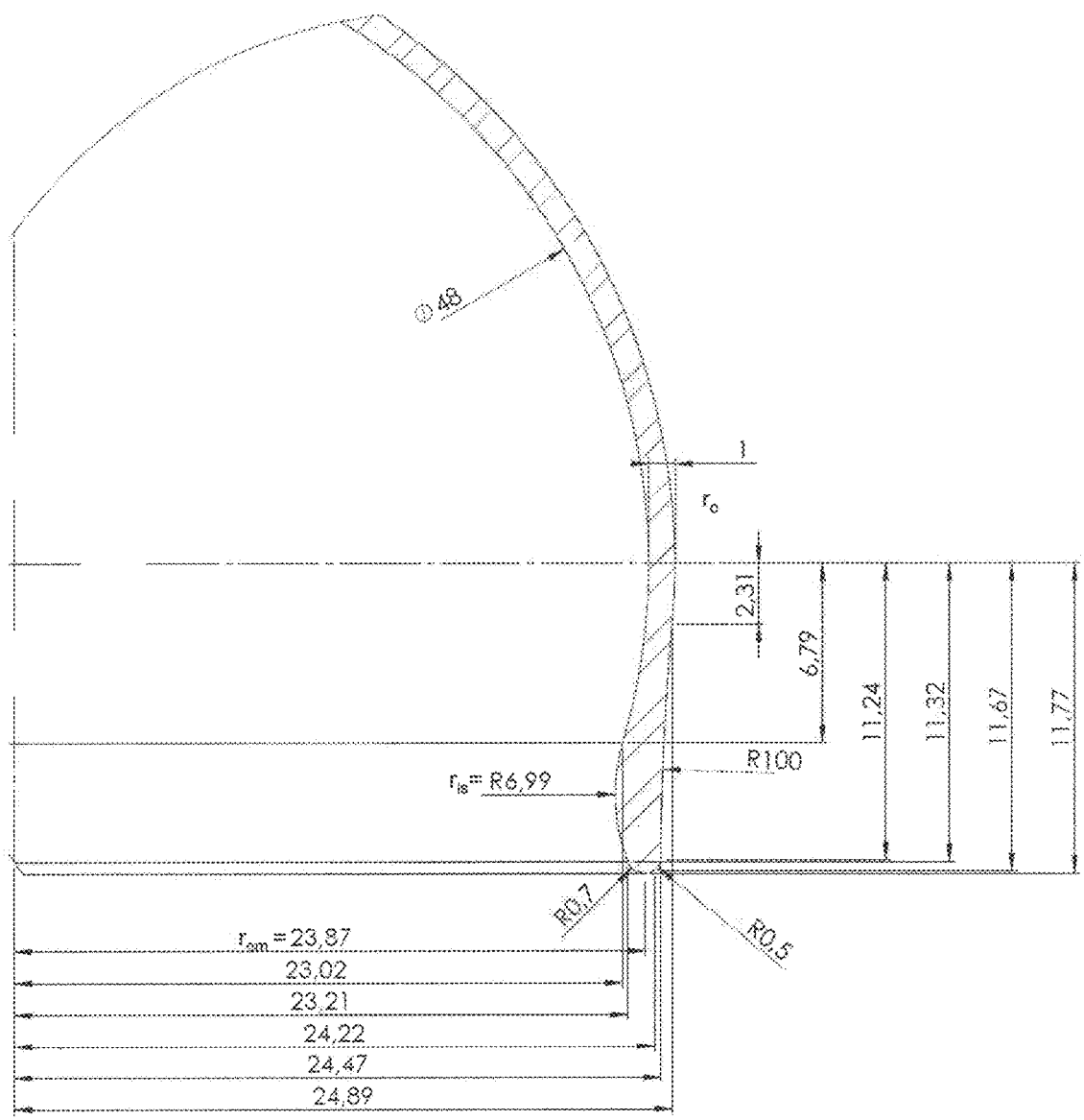
FIG. 4*a* shows a close-up of the implant in FIG. 1 sized to a human femoral head and illustrating the details of the skirt zone and the collar of the implant.

An exemplary embodiment of the presently disclosed medical implant adapted to a human patient is illustrated in FIG. 4a. The shell has an inner diameter of 48 mm, i.e. $r_s$=24 mm. $r_{om}$=23.87 mm and $r_o$=22.733 mm (illustrated in FIG. 5a). The thickness of the shell above the equatorial plane is 1 mm, whereas the maximum thickness of the shell at the skirt zone is 1.74 mm. The first position 10 is 6.79 mm vertically below the equatorial plane corresponding to 16.4 degrees below the equatorial plane, whereas the second position 11 is 2.31 mm below the equatorial plane corresponding to 5.3 degrees below the equatorial plane. The skirt zone is formed by $R_1$=6.99 mm, $R_2$=0.7 mm, $R_3$=0.5 mm and $R_4$=100 mm. As can be deduced from FIG. 4a $r_o/r_{om}$=0.952, $r_s/r_o$=1.056, $r_{om}/r_s$=0.995, $h_1/r_s$=1.49 and $h_1/h_2$=3.04.

Figure 4B:
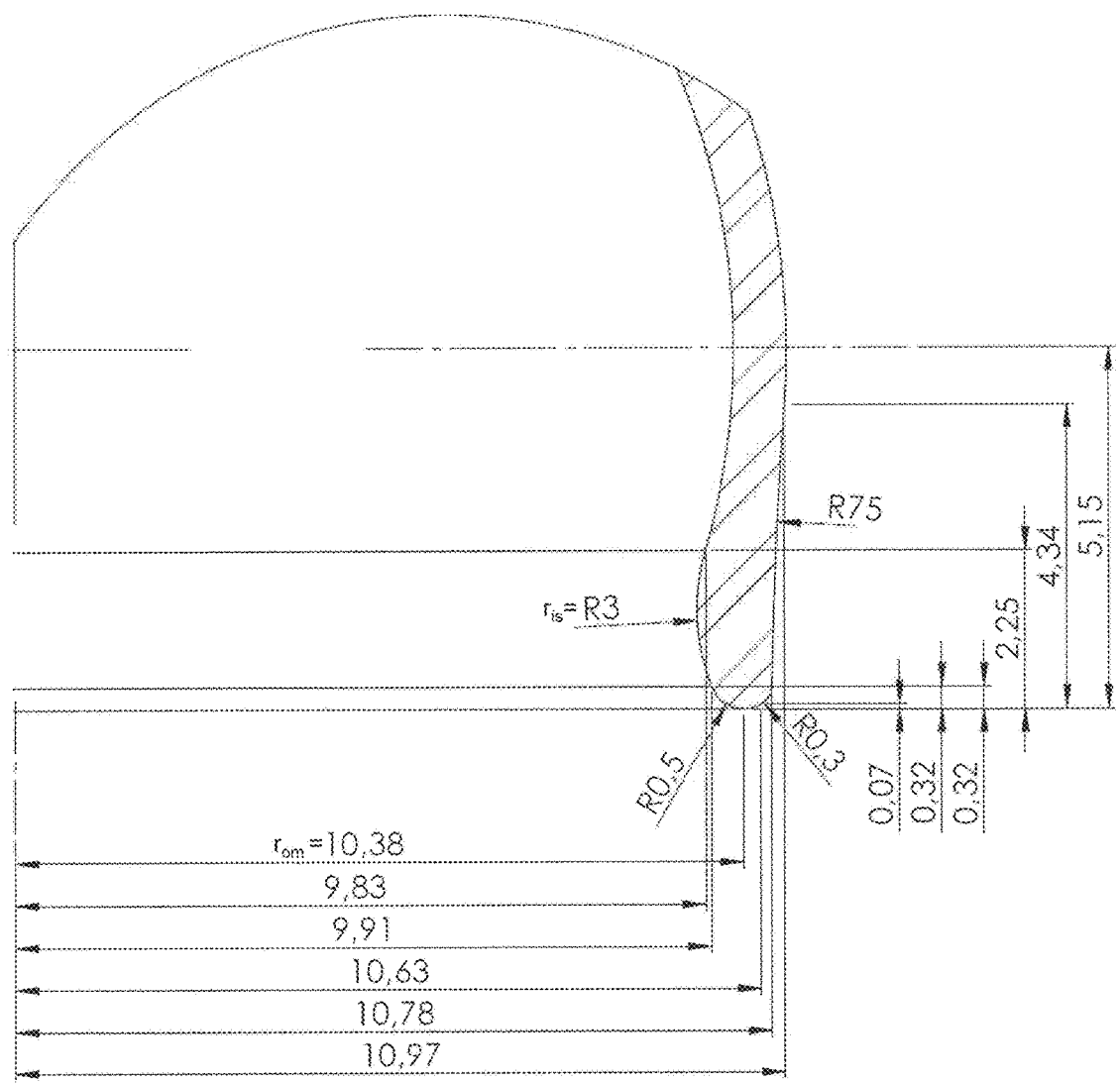
FIG. 4*b* shows a close-up of the implant in FIG. 1 sized to a femoral head of a dog and illustrating the details of the skirt zone and the collar of the implant.

A corresponding illustration of an implant adapted to a dog is illustrated in FIG. 4b with $r_o$ illustrated in FIG. 5b. The size of the two implants from FIGS. 4a and 4b are compared in FIG. 6. The shell in FIG. 4b has an inner diameter of 20.5 mm, i.e. $r_s$=10.25 mm. $r_{om}$=10.38 mm and $r_o$=9.709 mm (illustrated in FIG. 5b). The thickness of the shell above the equatorial plane is 0.75 mm, whereas the maximum thickness of the shell at the skirt zone is 1.07 mm. The first position 10 is 2.9 mm vertically below the equatorial plane corresponding to 16.4 degrees below the equatorial plane, whereas the second position 11 is 0.81 mm below the equatorial plane corresponding to 4.2 degrees below the equatorial plane. As can be deduced from FIG. 4b $r_o/r_{om}$=0.935, $r_s/r_o$=1.056, $r_{om}/r_s$=1.012, $h_1/r_s$=1.49 and $h_1/h_2$=2.99. The design principle in the two implants in FIGS. 4a and 4b are the same, but due to the difference in thickness of the two implants not all the relative parameters are the same. However, at least the factor $r_s/r_o$ and the first position at the inner surface (16.4 degrees below the equatorial plane) is the same for both implants.

FIG. 7 shows a cross-sectional view of the implant in FIGS. 4b and 5b impinging upon a sphere with a radius equal to the inner radius $r_s$ of the shell of the implant. This resembles the situation of the implant impinging the almost spherical femoral head. The resulting angle of attack of the implant upon the sphere is only 17 degrees as illustrated in the drawings due to the configuration of the skirt zone and the orifice of the implant. The change in curvature of the skirt zone provides an orifice of the shell with sloping sides, i.e. the inner surface of the implant slopes outwards through the orifice, and these sloping sides fits well with the outer curvature of the sphere. For the presently disclosed medical implant to actually be mounted on a femoral head with a diameter that corresponds to the inner diameter $2r_s$ of the shell, either the implant or the femoral head (or both) must provide some flexibility during insertion. If a force is applied vertically downwards to the top of the implant when impinging upon a sphere as illustrated in FIG. 7, this force is distributed to the area of contact between the sphere and the implant. The configuration of the skirt zone and the orifice of the implant thereby ensure that either the skirt zone of the implant is pressed outwards or the sphere is compressed from the side during insertion (or both). The present inventors have realized that the femoral head can provide a sufficient elasticity during insertion of the present implant, if an instant force, like a stroke or sudden impact, is applied to the top of the implant. It further helps that the femoral head is like a compressed sphere when seen from the side as illustrated in FIG. 12.

Figures 11, 12:
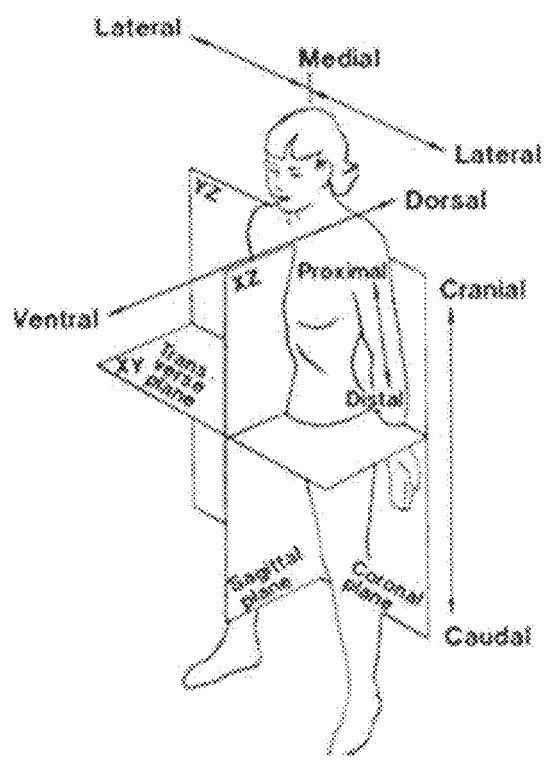
FIG. 11 shows the planes relevant for x-ray determination of the size of the femoral head.
FIG. 12 shows part of the femur.

FIG. 12 shows a part of a femur with the femoral head and femoral neck. The direction of the motion of the implant during the attachment process is indicated by arrow M. As the diameter of the femoral head indicated by F1 is smaller than diameter indicated by F2 the implant can be forced onto the femoral head by a sliding motion. The same geometry insures that the implant is not accidentally detached when first attached to the femoral head.

Figure 8A:
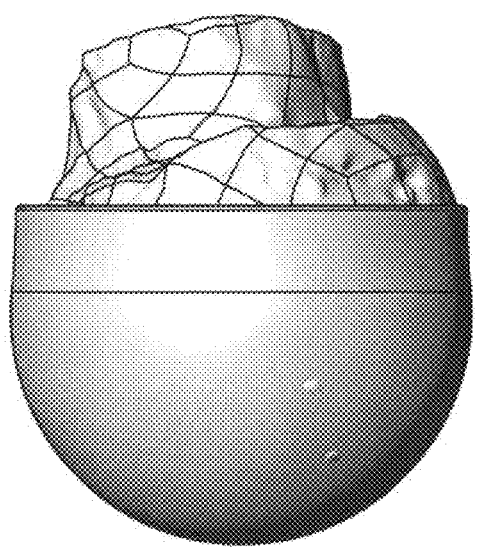
FIGS. 8*a-d* models the adaptation of the implant in FIG. 1 to a human femoral head.
Figure 8B:
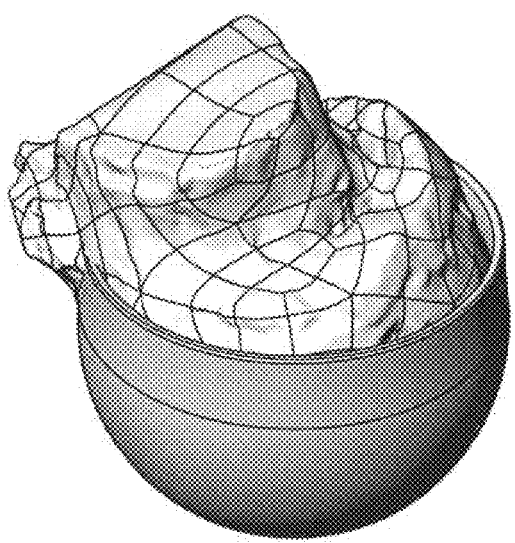
Figure 8C:
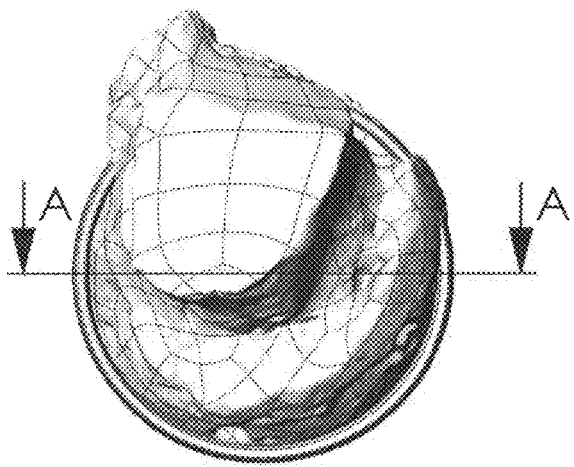
Figure 8D:
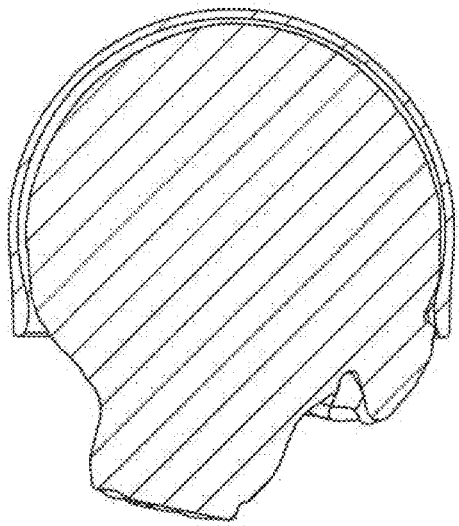

FIGS. 8a-c show 3D models of the adaptation of the implant in FIG. 1 attached to a human femoral head. It is seen that this embodiment provides an almost smooth surface towards the acetabulum (not shown) with a very small outer collar, however still providing sufficient fixation of the implant at the femoral head due to the inner collar. This can be seen from the cross-sectional view in FIG. 8d taken along the line A-A in FIG. 8c.

FIGS. 9 and 10 show another embodiment of the presently disclosed implant. The perspective view in FIG. 9a show the implant 1' comprising a dome shaped shell 2' having an orifice surrounded by a collar 4'. The shell 2' has an outer surface 5' and an inner surface 6'. The shell 2' is spherical above the collar 4. FIG. 9b shows a cross sectional view of the implant 1' in FIG. 9a. As for the embodiment shown in FIG. 3a the height $h_1$ of the shell is the distance from the apex of the inner surface of the shell to the plane of the maximum orifice radius $r_{om}$. The lower height $h_2$, is the distance from the equatorial plane containing the equatorial radius $r_s$ to the plane of the maximum orifice radius $r_{om}$. $h_o$ is the distance from the equatorial plane to the plane of the minimum orifice radius $r_o$. $r_o$ is the smallest orifice diameter and $r_{om}$ is the maximal orifice diameter.

FIG. 9c shows an enlargement of the section B indicated in FIG. 9b. The equatorial line is indicated by the stippled horizontal line. The skirt zone 4 is below the equator. The inner surface of the shell is spherical down to the first position 10'. At this first position the inner surface of the shell begins to curve in the opposite direction, i.e. the inner surface curved inwards whereas the skirt zone curves outwards, thereby forming an inner "collar" 9 by means of the curvature $R'_1$. The curvature $R'_1$ of the skirt zone "opens" the shell. The orifice is encircled by a rounded edge formed the radius of curvature $R'_2$. The outer surface of the shell is spherical to a second position 11 where the outer surface begins to curve in the opposite direction, i.e. outwards opposed to inwards, by means of the curvature $R'_4$. An outer collar 4' is formed by the curvature $R'_3$. The configuration of the first and second positions 10', 11' and the curvatures $R'_1$, $R'_2$, $R'_3$ and $R'_4$ forms the skirt zone of the shell and determines the varying thickness of the shell at the skirt zone.

Figure 9D:
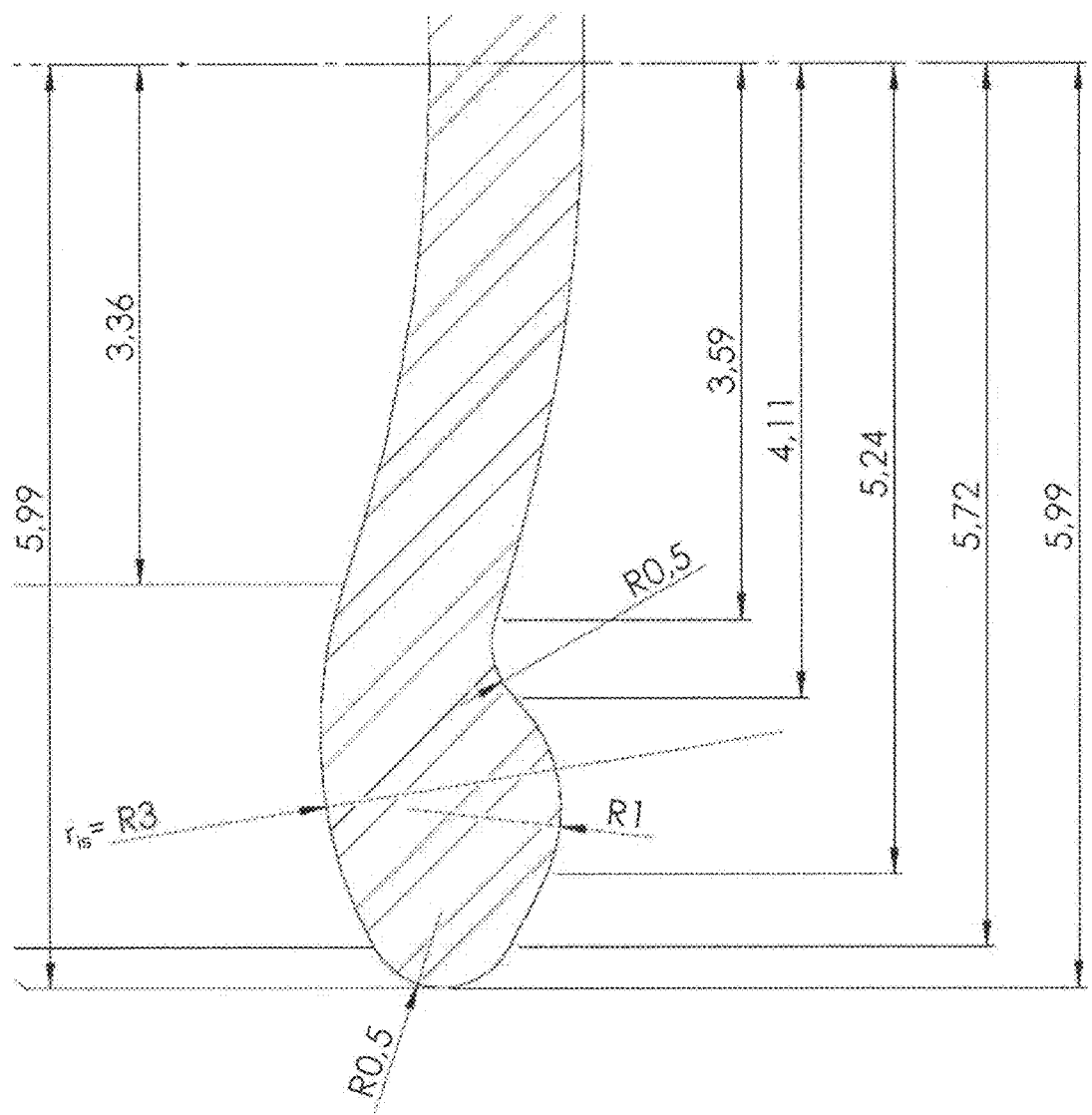
FIG. 9*d* shows a close-up of the implant in FIG. 9*a* sized to the femoral head of a dog and illustrating the details of the skirt zone and collar of the implant.

An exemplary second embodiment of the presently disclosed medical implant adapted to a dog is illustrated in FIG. 9d. The shell has an inner diameter of 21 mm, i.e. $r_s$=10.5 mm. The thickness of the shell above the equatorial plane is 0.75 mm. The first position 10 is 3.36 mm vertically below the equatorial plane, whereas the second position is 3.59 mm below the equatorial plane. The skirt zone is formed by $R_1$=3 mm, $R_2$=0.5 mm, $R_3$=1 mm and $R_4$=0.5 mm. I.e. compared to the first embodiment illustrated in detail in FIGS. 4a and 4b the second position in this second embodiment is below the first position.

It is seen that the collar 4' is thick relatively to the average shell thickness. As the inner radius $R'_1$ of the curvature of the inner surface of the collar is larger than the outer radius $R'_2$ of the outer surface of the collar, a transition curve with a small radius $R'_4$ is formed at the border between the main shell and the collar 4' whereby a circumferential shoulder 7' is created. The circumferential shoulder 7' can be used as an attachment point for tools and/or for preventing that the shell rotates too much i.e. prevents the collar from entering the zone between the femoral head and the acetabulum. The radius $R'_3$ of the rounded edge 8' is also relatively small compared to the inner radius $R'_1$ and outer radius $R'_2$. The implant has a shell thickness D of the spherical part of the shell.

Figure 10A:
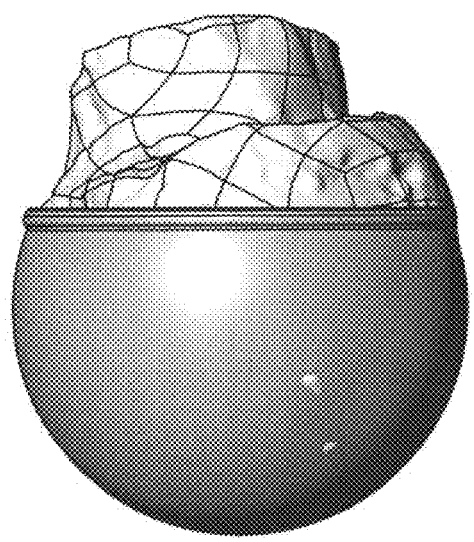
Figure 10B:
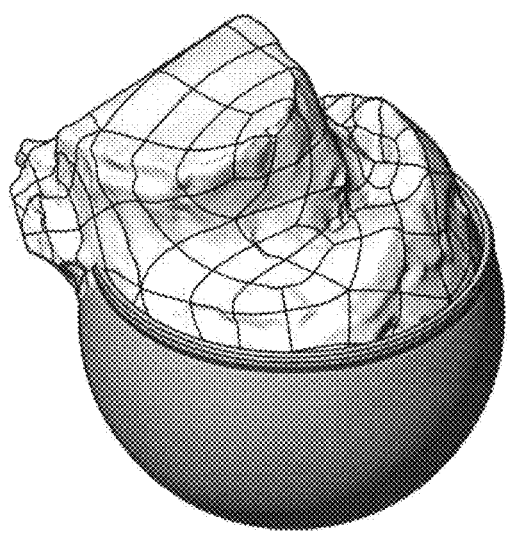
Figure 10C:
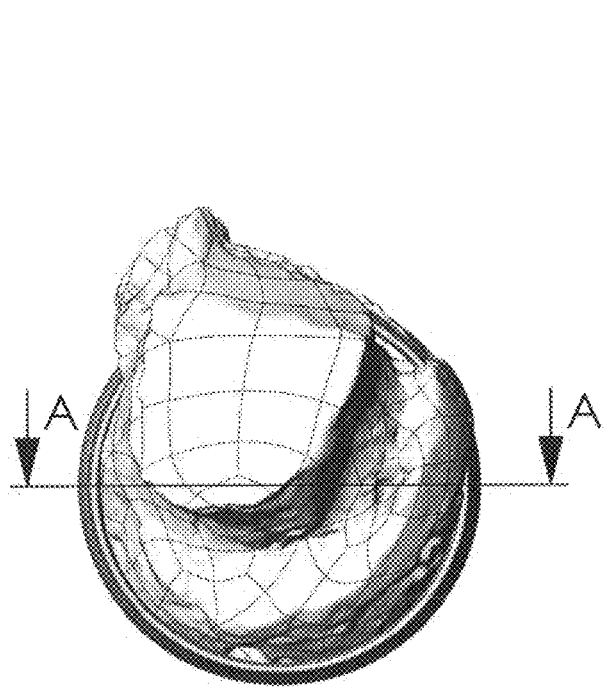
Figure 10D:
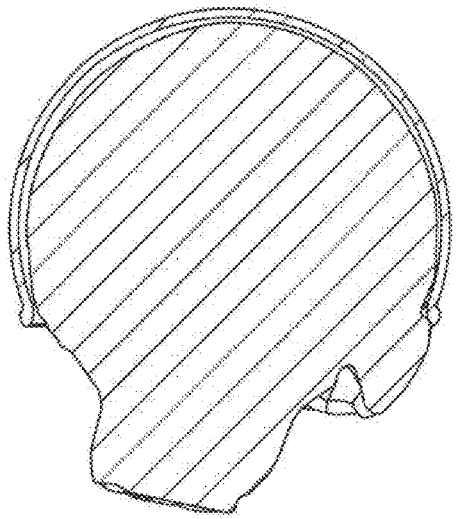

FIGS. 10a-c show 3D models of the adaptation of the implant in FIG. 9 attached to a human femoral head. It is seen that this embodiment provides a larger outer collar that may help to attach the implant to the femoral head. The cross-sectional view in FIG. 10d is taken along the line A-A in FIG. 10c.

FIG. 11 shows the coronial plane and the sagittal plane of the human body. X-ray images can be taken along these planes in order to be able to determine the largest diameter of the femoral head and thereby select an implanting with a matching size.

Figure 13:
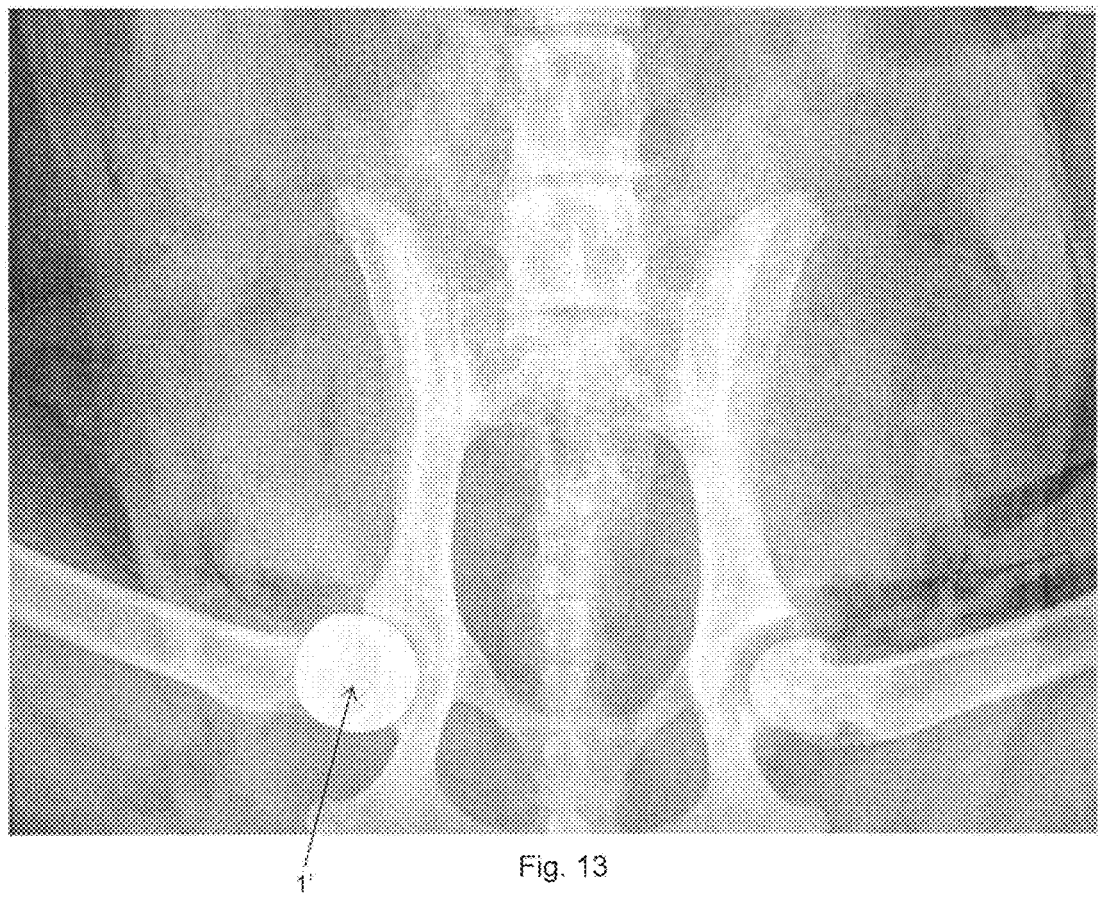
FIG. 13 shows an x-ray of the hip area of a dog with an implant according to the present disclosure.
Figure 14A:
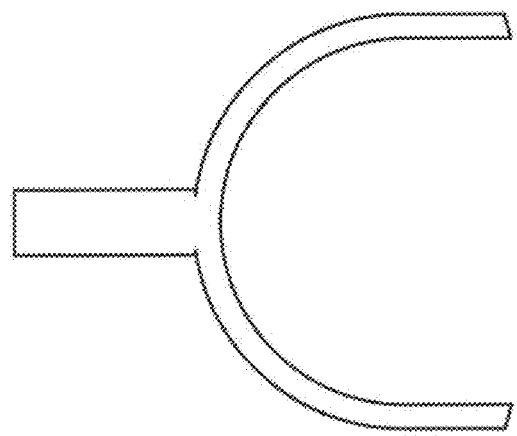
FIG. 14A shows an extended dome form with internal cutting flutes to shape femoral head to match implant.
Figure 14B:
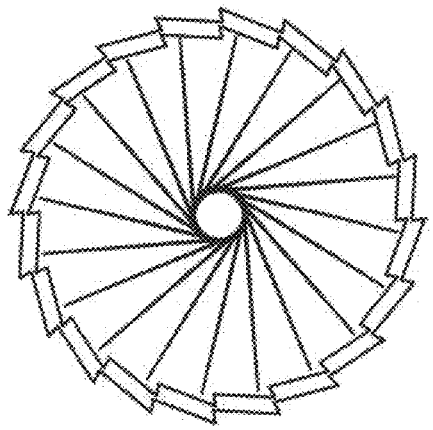
FIG. 14B is an illustration of a femoral head reamer, with cutting edges to remove large osteophytes around femoral neck.

FIG. 13 shows an x-ray of the hip area of a dog seen from the front, i.e. it is a frontal X-ray of the Coronal plane. The implant 1' is clearly seen to cover the femoral head and be received in the acetabulum.

Surgical Approach

In the following a method for surgically inserting the presently disclosed medical implant will be described. The approach is based on the 'Approach to the craniodorsal and caudodorsal aspects of the hip joint by osteotomy of the greater trochanter' described in Piermattei's Atlas of Surgical Approaches to the Bones and Joints of the Dog and Cat (3rd Ed).

1. Skin incision centred over the greater trochanter of the femur, extending distally to the mid-femoral level. Subcutaneous tissues are separated along the same line.
2. The cranial border of the biceps femoris muscle is freed allowing caudal retraction of this muscle.
3. The deep fascia and muscles cranial to the greater trochanter and metaphysis are freed.
4. The gluteal muscles are identified and an instrument placed medial to the insertions of the deep and middle gluteal muscles, to identify the depth of the subsequent osteotomy.
5. The greater trochanter is osteotomised and reflected dorsally.
6. The dorsal joint capsule is incised as laterally as possible and this incision is extended caudally and cranially to expose the joint surfaces while preserving as much tissue for suturing as possible.
7. The articularis coxae muscle is freed from the cranial aspect of the femoral neck.
8. The teres ligament is sectioned using scissors or meniscal knife while tensioning the ligament by external rotation of the femur. Additional joint capsule is incised as needed to permit luxation of the femoral head.
9. While externally rotating and caudally displacing the femoral head, the iliopsoas muscle insertion is palpated deep to the femoral neck and ventral to the acetabulum.
10. The muscle and tendon of insertion is bluntly dissected free, and an instrument passed behind the muscle before sectioning.
11. A Hohmann retractor is placed caudal to the acetabulum and used to lever the femur caudally, exposing the acetabulum for reaming.
12. The femur is externally rotated and retractors used to protect the surrounding muscles prior to femoral head reaming.
13. The implant is placed on the shaped femoral head and the coxofemoral joint is reduced.
14. The dorsal joint capsule is sutured.
15. The osteotomy is closed using a pin and tension band technique.
16. Remaining layers are closed routinely.
17. A hobble is placed between the hind limbs to prevent excessive limb movement in the first two weeks in order to reduce the risk of luxation (particularly ventrally).

Removing the ventral joint capsule may make the patient prone to ventral luxation. Exercise restriction and use of hobbles will be advisable in the first 2 weeks post-surgery. The femoral head is commonly distorted due to the prevalence of hip dysplasia in our patient groups. Some form of femoral head reamer will simplify implant placement and sizing (into 2-4 mmm steps or small/medium/large). The Copeland shoulder implant reamer is similar to what would be needed.

The invention claimed is:

1. A medical implant for attachment to and at least partly covering the femoral head of a subject, said medical implant comprising a dome shaped metallic shell with a skirt zone below the equatorial plane having an unbroken circular orifice at the lowest part of the implant defining the only entrance opening of the implant, said shell having an inside surface and an outside surface, a height $h_1$, an inner equatorial shell radius $r_s$ and an inner orifice radius $r_o$ wherein the shell radius $r_s > r_o$, and $h_1 > r_s$ the entire inside surface of the shell and the entire outside surface of the shell are spherical at least above the equatorial plane, the unbroken circular orifice is defined by a circumferential rounded edge, and the medical implant is configured for at least initial unconstrained attachment to the unshaped natural femoral head such that the implant is free to rotate relative to the natural femoral head initially after insertion of the medical implant in the subject.

2. The medical implant according to claim 1 wherein the dome is a spherical dome.

3. The medical implant according to claim 1, wherein the outer surface of the shell of at least a part of said skirt zone has a different curvature than the curvature of the outer surface of the shell above the equatorial plane.

4. The medical implant according to claim 1, wherein the inside surface of the shell is spherical above a first position at said inside surface below the equatorial plane.

5. The medical implant according to claim 4, wherein said first position is an inflection point of the inner surface.

6. The medical implant according to claim 4, wherein the inner surface curves in the opposite direction below said first position.

7. The medical implant according to claim 4, wherein said first position is located less than 20° below the equatorial line.

8. The medical implant according to claim 4, wherein said first position is located at least 5° below the equatorial line.

9. The medical implant according to claim 4, wherein the radius of curvature of the inner surface of the shell changes from $r_s$ to $r_{is}$ at said first position, and wherein $r_s/r_{is}$ is between 3 and 3.8.

10. The medical implant according to claim 1, wherein the outside surface of the shell is spherical above a second position at said outside surface below the equatorial plane.

11. The medical implant according to claim 10, wherein said second position is an inflection point of the outer shell surface.

12. The medical implant according to claim 10, wherein the outer surface curves in the opposite direction below said second position.

13. The medical implant according to claim 10, wherein said second position is located less than 20° below the equatorial plane.

14. The medical implant according to claim 10, wherein said second position is located at least 1° below the equatorial plane.

15. The medical implant according to claim 10, wherein said second position is located at least 15° below the equatorial plane.

16. The medical implant according to claim 1, wherein the diameter $2r_o$ of the orifice is at least 4% smaller than the inner equatorial diameter $2r_s$ of the shell.

17. The medical implant according to claim 1, wherein the rounded edge forms a collar encircling the orifice.

18. The medical implant according to claim 1, wherein the inside of the rounded edge is curving outward to form an orifice with a maximum diameter $2r_{om}$ and a minimum diameter $2r_o$.

19. The medical implant according to claim 18, wherein the maximum diameter of the orifice $2r_{om}$ is equal to the inner equatorial diameter $2r_s$ of the shell.

20. The medical implant according to claim 18, wherein $r_{om}/r_s$ is between 0.98 and 1.02.

21. The medical implant according to claim 18, wherein $r_o/r_{om}$ is less than 0.96.

22. The medical implant according to claim 1, wherein the thickness of the shell is constant at least above the equatorial diameter.

23. The medical implant according to claim 1, wherein the thickness of at least a part of the skirt zone of the shell varies.

24. The medical implant according to claim 1, wherein the thickness of the shell is thicker near the rounded edge than at an apex at a top part of the shell.

25. The medical implant according to claim 1, wherein the shell is manufactured in a steel alloy, in 316 LVM steel, in a cobalt/chromium alloy, or in a titanium alloy.

26. The medical implant according to claim 1, wherein the inner surface of the shell of at least a part of said skirt zone has a different curvature than the curvature of the inner surface of the shell above the equatorial plane.

27. The medical implant according to claim 1, wherein the shell is thicker near the circumferential rounded edge than at an apex at a top part of the shell.

28. The medical implant according to claim 1, wherein the entire inside surface of the shell and/or the entire outside surface of the shell are smooth at least above the equatorial plane.

29. The medical implant according to claim 10, wherein the entire inside surface of the shell and/or the entire outside surface of the shell are smooth at least above the equatorial plane.

* * * * *